(12) United States Patent
Chen et al.

(10) Patent No.: US 10,823,666 B2
(45) Date of Patent: Nov. 3, 2020

(54) IN-VITRO OPTICAL TRANSMITTANCE TEST OF LED ON ORAL TISSUE

(71) Applicant: Indiana University Research and Technology Corporation, Indianapolis, IN (US)

(72) Inventors: Jie Chen, Carmel, IN (US); Feifei Jiang, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/470,717

(22) PCT Filed: Dec. 15, 2017

(86) PCT No.: PCT/US2017/066559
§ 371 (c)(1),
(2) Date: Jun. 18, 2019

(87) PCT Pub. No.: WO2018/118666
PCT Pub. Date: Jun. 28, 2018

(65) Prior Publication Data
US 2019/0339195 A1    Nov. 7, 2019

Related U.S. Application Data

(60) Provisional application No. 62/436,146, filed on Dec. 19, 2016.

(51) Int. Cl.
*G01N 21/31* (2006.01)
*A61B 5/00* (2006.01)
(Continued)

(52) U.S. Cl.
CPC .......... *G01N 21/31* (2013.01); *A61B 5/0088* (2013.01); *A61B 5/4552* (2013.01);
(Continued)

(58) Field of Classification Search
CPC ............ A61B 5/14551; A61B 5/14552; A61B 5/1495; A61B 5/0088; A61B 5/4552;
(Continued)

(56) References Cited

U.S. PATENT DOCUMENTS

| | | | |
|---|---|---|---|
| 5,420,687 A | 5/1995 | Kachanov | |
| 6,603,554 B1 * | 8/2003 | Eisenberg | G01N 21/57 356/239.1 |

(Continued)

OTHER PUBLICATIONS

PCT/US2017/066559; Indiana University Research and Technology Corporation; International Search Report and Written Opinion dated Feb. 20, 2018.

*Primary Examiner* — Hoa Q Pham
(74) *Attorney, Agent, or Firm* — Faegre Drinker Biddle & Reath LLP (57) ABSTRACT

A method for determining a transmittance of light on oral tissue is provided, comprising: providing an LED; directing light from the LED onto a sample of oral tissue; measuring a first power of the light at a first surface of the sample; measuring a second power of the light at a second surface of the sample; computing surface loss of the light; and determining the transmittance of the light using the first power, the second power, and the surface loss.

12 Claims, 8 Drawing Sheets

(51) Int. Cl.
*A61N 5/06* (2006.01)
*G01N 21/59* (2006.01)

(52) U.S. Cl.
CPC ........... *A61N 5/0603* (2013.01); *G01N 21/59* (2013.01); *A61N 2005/0606* (2013.01); *A61N 2005/0659* (2013.01)

(58) Field of Classification Search
CPC ........... G01J 1/32; G01N 21/31; G01N 21/59; A61N 5/0603; A61N 2005/0606; A61C 19/04; A61C 7/08; A61C 7/008; A61C 1/0046
USPC ........... 356/432–440; 600/31, 331, 332, 334, 600/407; 250/205, 552; 73/655
See application file for complete search history.

(56) References Cited

U.S. PATENT DOCUMENTS

| | | | |
|---|---|---|---|
| 7,087,887 B1* | 8/2006 | Pi | G02B 6/2826 250/227.14 |
| 2005/0105095 A1 | 5/2005 | Pesach et al. | |
| 2007/0015981 A1 | 1/2007 | Benaron et al. | |
| 2009/0103085 A1 | 4/2009 | Hu | |
| 2011/0052207 A1* | 3/2011 | Ishikawa | H01S 5/0687 398/182 |
| 2011/0270071 A1 | 11/2011 | Furukawa | |
| 2014/0072932 A1 | 3/2014 | Brawn et al. | |
| 2016/0054281 A1* | 2/2016 | Smeeton | G01N 21/532 250/373 |
| 2016/0097716 A1 | 4/2016 | Gulati et al. | |
| 2018/0177570 A1* | 6/2018 | Alauddin | A61C 7/08 |
| 2019/0017872 A1* | 1/2019 | Brunson | G01J 3/4406 |

* cited by examiner

IN-VITRO OPTICAL TRANSMITTANCE TEST OF LED ON ORAL TISSUE

CROSS-REFERENCE TO RELATED APPLICATIONS

The present application is a 35 U.S.C. § 371 national phase application of International Application Serial No. PCT/US2017/06659, filed Dec. 15, 2017, which claims priority to U.S. Provisional Application Ser. 62/436,146, entitled "IN-VITRO OPTICAL PENETRATION TEST OF LED ON ORAL TISSUE," filed on Dec. 19, 2016, the entire disclosure of which being expressly incorporated herein by reference.

FIELD OF THE DISCLOSURE

The present disclosure generally relates to photobiomodulation ("PBM") therapy, and more particularly to determining transmittance of light on oral tissue.

BACKGROUND

PBM stimulates cells and regulates cell activities. However, the dose the cell senses is still unknown because the transmittances of the light on various tissues are not available. As such, a need exists for an in-vitro optical transmittance test, in particular for oral tissue.

SUMMARY

According to one embodiment, the present disclosure provides a method for determining a transmittance of light on tissue, comprising: providing a light source; directing light from the light source onto a sample of tissue; measuring a first power of the light at a first surface of the sample; measuring a second power of the light at a second surface of the sample; computing a surface loss of the light; and determining the transmittance of the light using the first power, the second power, and the surface loss. In one aspect of this embodiment, the transmittance of light is represented by an attenuation coefficient in the Beer-Lambert law. In a variant of this aspect, determining the transmittance includes computing the transmittance according to $T = \emptyset_T/\emptyset_0 (1-r) = e^{-\alpha l}$ where T is the transmittance without the surface loss, $\emptyset_T$ is a radiant flux of the second power of the light at the second surface of the sample, $\emptyset_0$ is an incoming radiant flux, r is the surface loss rate, $\alpha$ is the attenuation coefficient, and l is a thickness of the sample. This formula is based on the original formula of the Beer-Lambert Law, $=\emptyset_T/\emptyset_0 = e^{-\alpha l}$, modified by adding a coefficient (1−r) for removing the effects of surface loss on the real transmittance through the tissues. In a further variant, the first surface of the sample is directed toward the light source and the second surface of the sample is directed away from the light source. In another aspect, the light source is an LED. In still another aspect, the tissue is oral tissue. In yet another aspect of this embodiment, directing light from the light source includes directing light having a wavelength between about 420 nm and about 1050 nm.

According to another embodiment, the present disclosure provides a system for determining a transmittance of light on tissue, comprising: a light source that emits light; a wavelength/power meter having an input window, the wavelength/power meter being configured to measure the wavelength, a first power of the emitted light at a first surface of a sample of the tissue positioned at the input window and a second power of the emitted light at a second surface of the sample. The measurements are used to compute a surface loss of the emitted light onto the sample and to determine the transmittance of the emitted light into the sample using the first power, the second power and the surface loss. One aspect of this embodiment further comprises a spectroscope having an input to receive light from the light source and output that emits the emitted light at a desired wavelength. Various wavelengths ranging from 420 nm to 1050 nm were used. In still another aspect, the transmittance of the emitted light is represented by an attenuation coefficient in the Beer-Lambert law. In yet another aspect, wherein the tissue is oral tissue. In a further aspect of this embodiment, the transmittance was completed according to $T = \emptyset_T/\emptyset_0 = (1-r) e^{-\alpha l}$ where T is the transmittance without the surface loss, $\emptyset_T$ is a radiant flux of the second power of the light at the second surface of the sample, $\emptyset_0$ is an incoming radiant flux, r is the surface loss rate, $\alpha$ is an attenuation coefficient, and l is a thickness of the sample. In a further aspect, the first surface of the sample is directed toward the light source and the second surface of the sample is directed away from the light source.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings, wherein.

Although the drawings represent embodiments of the various features and components according to the present disclosure, the drawings are not necessarily to scale and certain features may be exaggerated in order to better illustrate and explain the present disclosure. The exemplification set out herein illustrates embodiments of the disclosure, and such exemplifications are not to be construed as limiting the scope of the disclosure in any manner.

DETAILED DESCRIPTION OF EMBODIMENTS OF THE DISCLOSURE

For the purpose of promoting an understanding of the principles of the disclosure, reference will now be made to the embodiments illustrated in the drawings, which are described below. It will nevertheless be understood that no limitation of the scope of the disclosure is thereby intended. The disclosure includes any alterations and further modifications in the illustrated device and described methods and further applications of the principles of the disclosure, which would normally occur to one skilled in the art to which the disclosure relates. Moreover, the embodiments were selected for description to enable one of ordinary skill in the art to practice the disclosure.

The present disclosure is directed to determining the transmittances of light into oral tissues. Tissue samples of gum, cortical bone and trabecular bone were prepared from ten Yucatan pigs' mandibles. The transmittance was represented by the attenuation coefficient in the Beer-Lambert law. Higher attenuation coefficient means lower transmittance. The samples were tested under the light at wavelengths from 420 nm to 1050 nm. The light power on both sides of the samples was used to calculate the transmittance. The results showed that the Beer-Lambert law can estimate the transmittance after elimination of the surface loss. The gum has the highest attenuation coefficient and the trabecular bone has the lowest. The attenuation coefficient is higher at lower wavelengths for all three tissues, and is lower and kept plateaued at wavelengths from about 700 nm to about 1050 nm. The light power within the tested range does not appear to affect the transmittance.

PBM has been found to have multiple clinical benefits, which include reducing pain, improving wound healing, accelerating bone healing, promoting osteointegration, facilitating orthodontic tooth movement, stimulating bone formation and healing, improving periodontal tissue repair, and decreasing inflammation and root resorption. The lighting sources referenced herein are lasers or light-emitting diodes ("LEDs"). Compared to a laser, an LED could be less expensive.

There are also controversies on the biological effects PBM. Some research has indicated that PBM using LEDs does not stimulate tooth movement while PBM using lasers does. Other research indicates that significantly different fibroblast proliferations occur when applying PBM with different wavelengths. However, different light intensity, stimulation duration, and wavelength had been used in previous studies. The inconsistency of the experimental settings, especially the stimulatory intensity and duration (dose), of these studies may lead to the inconsistent outcomes and difficulty for comparison.

The biological reactions are cell activities that are initiated by the light energy. The effects are likely dependent on the energy level, or dose, received by the cells. The dose relies on the amount of light that penetrates into the tissues and the transmittance of the tissues. Previous animal studies performed on different subjects used different ways to apply the light with different intensities and durations. There was no report on the minimum dose that triggers the cell response. In these studies, only the lighting source power or the energy on the surface was reported. The light was delivered using various techniques, which affected the amount of energy that penetrated into the tissue. Furthermore, the energy on cells is still unknown because the transmittance of the light of various tissues has not been reported. These factors made the results incompatible. Individual tissue may have its own transmittance. To estimate the dose on a cell, it is important to control the light that penetrates into the tissue and to determine the transmittances of the biological tissues as well as their combinations so that the dose on the cell can be estimated.

According to the teachings of the present disclosure, 1) a method to experimentally determine the transmittance in terms of attenuation coefficient of biological tissues may be developed; 2) the effects of wavelength on the transmittance may be determined; 3) the transmittances of gum, cortical bone and cancellous bone of pig samples may be obtained; and 4) the use of the Beer-Lambert law on multiple tissue complex may be validated.

Materials and Methods

Figure 1A:
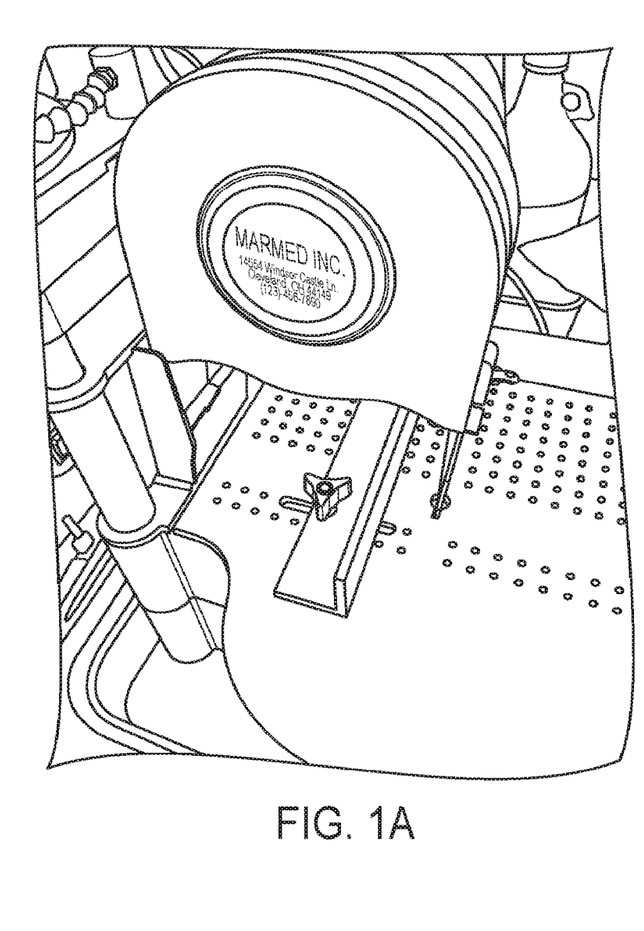
FIGS. 1A and 1B are perspective views of devices used for sample preparation.
Figure 1B:
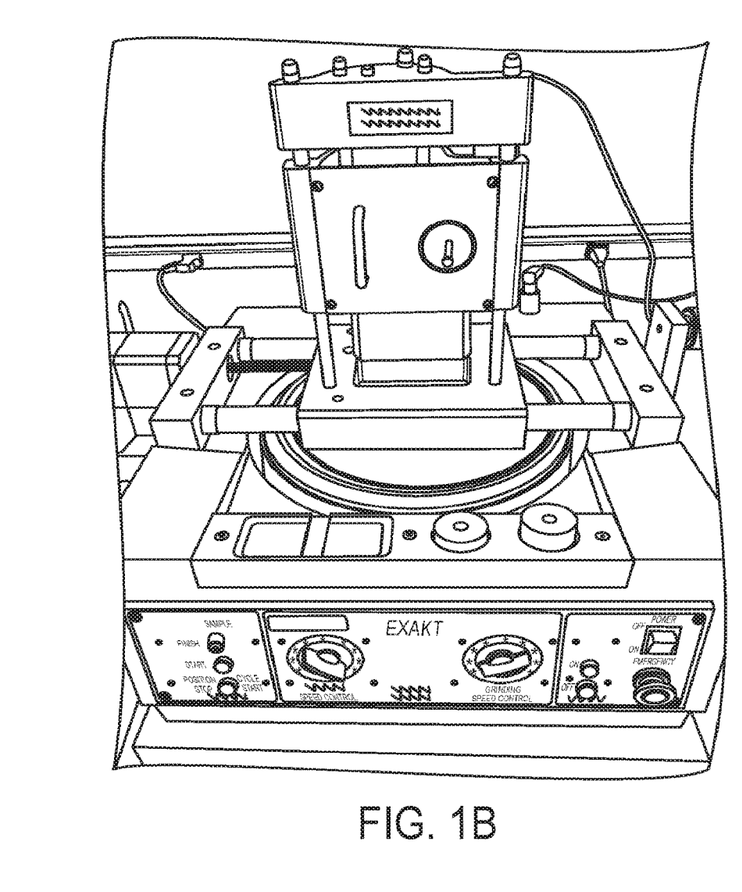
Figure 2A:
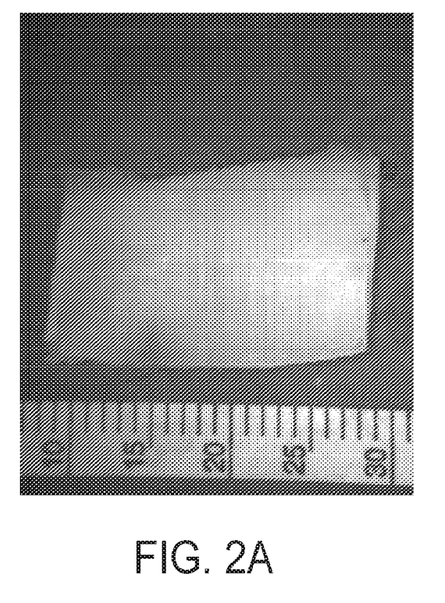
FIGS. 2A-C are perspective views of samples of bone and gum.
Figure 2B:
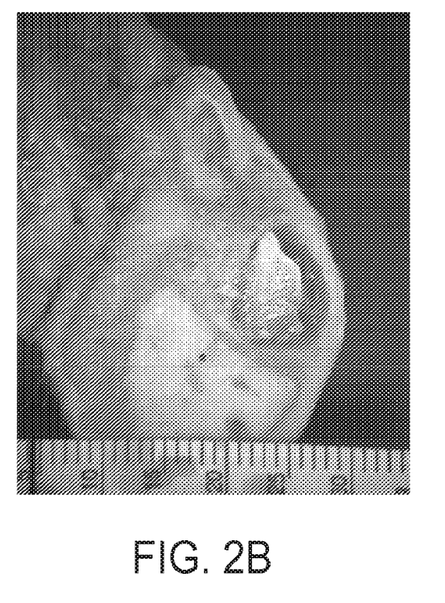
Figure 2C:
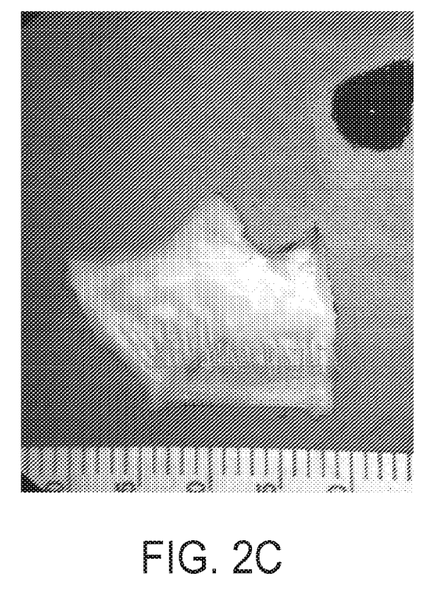

Samples of gum, cortical bone and trabecular bone from four Yucatan pigs' mandibles were used in this study. The samples were prepared by using a Bone Band Saw (such as manufactured by Mar-Med Inc. of Cleveland, Ohio) and an Exakt grinding system (such as manufactured by EXAKT Technologies, Inc. of Oklahoma City, Okla.) as shown in FIGS. 1A and 1B. The cortical and trabecular bones were cut into rectangular flat pieces with a thickness of around 1 mm (see FIG. 2A). The thickness of bone was measured using a caliper before testing. The gum was separated from the bone using a surgical blade. The thickness of the gum was measured from the sample section before separation (see FIGS. 2B and 2C).

The samples were tested by applying a light with a specified wavelength and power to an optical power meter with and without the tissue sample attached on the input window of the optical power meter as is further described below. Any light source (such as a laser or LED) that can control the wavelength and power can be used to determine the transmittance. The data described herein was obtained using the following experimental setups. Two experimental systems described below were built to test the transmittance of the sample tissues—one corresponding to a low wavelength range (420 nm to 700 nm) and another corresponding to a high wavelength range (780 nm, 850 nm, 940 nm, and 1050 nm). The systems consisted of an optical table, a lens (such as Ø1" N-BK7 Bi-Convex Lenses manufactured by Thorlabs Inc. of Newton, N.J.), a spectroscope, and a power/wavelength meter (such as Optical Power and Wavelength Meter OMM-6810B, Silicon Power/Wavehead OMH-6722B, ILX manufactured by Lightwave Corporation of Bozeman, Mont.). The light sources used in this study were an epoxy-encased LED centered at 780, 850, 940, and 1050 nm (manufactured by Thorlabs Inc. of Newton, N.J.) for higher wavelengths and a 100 W white LED lamp for lower wavelengths.

Figure 3:
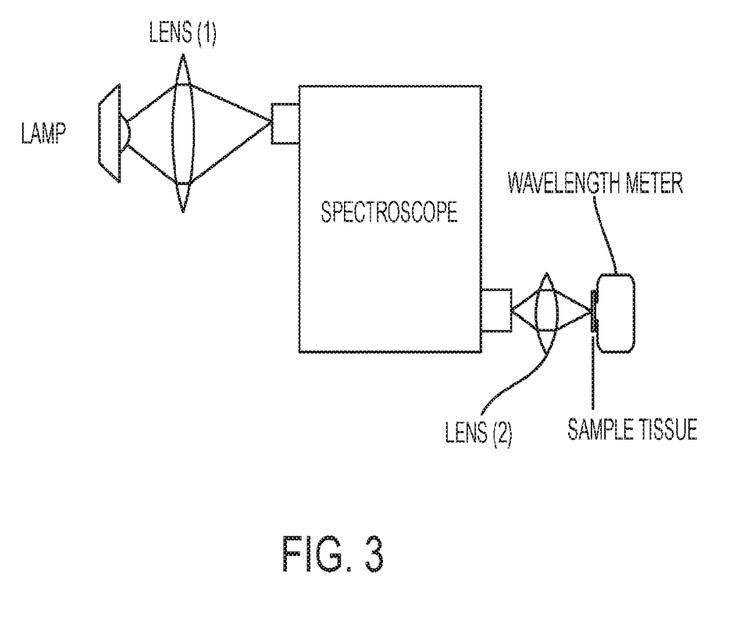
FIG. 3 is a schematic diagram of a system for testing the transmittance of light at lower wavelengths according to one embodiment of the present disclosure.

FIG. 3 shows the schematic of the system for testing the transmittance at low wavelengths of 420 nm to 700 nm. System 10 used 100 W white LED lamp 12 as the light source though lens 14, and the specified wavelengths of from 420 nm to 700 nm, in a 20 nm intervals, were kept by the spectroscope 16. Lens 13 and lens 14 are biconvex lenses that are used to focus the light to the spectroscope and the sample, respectively. The tissue sample 18 was placed at the input window 20 of the wavelength meter 22 so that the light power with or without sample 18 in the optical path could be measured. System 10 further includes a controller 24 coupled to wavelength meter 22 and configured to collect power and wavelength data to compute a surface loss of the light emitted by spectroscope 16 onto sample 18 and to determine a transmittance of the light into the sample 18 using the surface loss, a first power of the light measured at the surface of the sample 18 directed toward the spectroscope 16 and a second power of the light measured at the surface of the sample 18 directed away from the spectroscope 16. As explained below, three measurements were made to determine the attenuation coefficient and surface loss rate of a type of oral tissue: 1) the incoming light power with no sample attached on the power meter ($\varnothing_0$); 2) the transmitted light power with the first piece of sample attached on the power meter ($\varnothing_{1T}$); and 3) the transmitted light power with the first and second pieces of the same type of samples attached on the power meter ($\phi_{2T}$). The thickness, $l_1$ and $l_2$, had been measured before and e is a known constant. The resulting number is applied to equation (2) and (3) to calculate the attenuation coefficient ($\alpha$) and surface loss rate (r).

Figure 4:
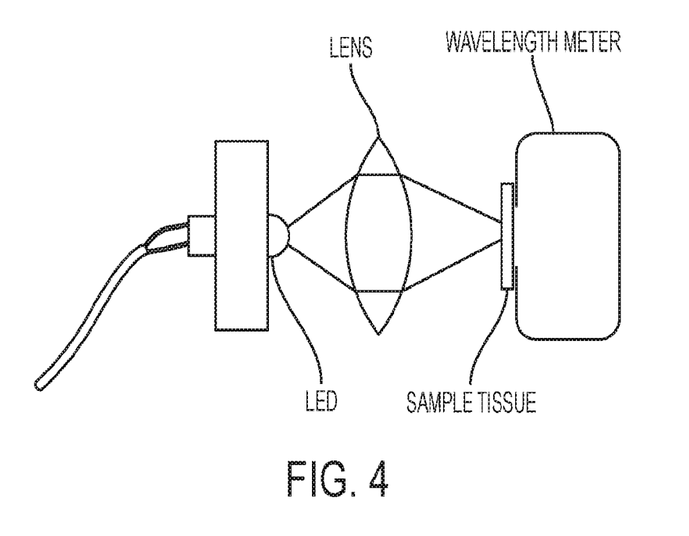
FIG. 4 is a schematic diagram of a system for testing the transmittance of light at higher wavelengths according to another embodiment of the present disclosure.

FIG. 4 shows the schematics of system 30 for testing the transmittance at higher wavelengths of 780, 850, 940, and 1050 nm. System 30 includes an infrared LED bulb 32 as a light source, a lens 34 and wavelength meter 22 having an input window 20. Four different LEDs were used with wavelengths centered at 780, 850, 940 and 1050 nm, respectively. The tissue sample 18 was placed at input window 20.

The systems 10, 30 were calibrated before testing. The tests were performed in a dark room so that the specimens were isolated from natural light. The wavelength meter 22 was zeroed right before the experiments to further reduce the error. The attenuation coefficient in the Beer-Lambert law was used to represent the level of intransparency of sample tissue 18 including gum, cortical bone and trabecular bone. While shining the light on the tissue samples 18, the input light power was reduced due to surface reflection and deflection, called surface loss, thus reducing the light power that penetrates into the tissues 18. The formulas shown below were modified based on the Beer-Lambert law to take the surface loss into consideration.

$$T = \frac{\phi_T}{\phi_0} = (1-r)e^{-\alpha l} \qquad (1)$$

T is the measured transmittance; $\phi_T$ is the radiant flux transmitted by the material, which represents the power measured on the back side of the tissue; $\phi_0$ is the incoming radiant flux, which represents the power measured without the sample tissue; r is the surface loss rate; $\alpha$ is the attenuation coefficient; and l is the path length (i.e., the thickness of sample 18).

It is assumed that the surface loss only occurs at the tissue-light interface, but not at the interface between two overlapped tissue samples. Then, the surface loss and the attenuation coefficient can be determined experimentally according to the following steps:
1. Two pieces of tissue sample 18 of the same material from the same animal were prepared. The thickness, $l_1$ and $l_2$, were measured.
2. The input light power, $\phi_0$, was measured using wavelength meter 22.
3. The first piece of tissue sample 18 was attached at input window 20 of wavelength meter 22 for the test. The optical power transmitted through the sample 18 was measured ($\phi_{1T}$).
4. The second piece of tissue sample 18 was attached on the back surface of the first piece. Then the optical power transmitted by the two pieces of material was measured ($\phi_{2T}$).
5. The attenuation coefficient ($\alpha$) and surface loss rate (r) of this material can be obtained by simultaneously solving the following two equations:

$$\frac{\phi_{1T}}{\phi_0} = (1-r_1)e^{-\alpha l_1} \qquad (2)$$

$$\frac{\phi_{2T}}{\phi_0} = (1-r_1)e^{-\alpha(l_1+l_2)} \qquad (3)$$

The solution is:

$$\alpha = \frac{1}{l_2}\ln\left(\frac{\phi_{1T}}{\phi_{2T}}\right) \qquad (4)$$

$$r_1 = 1 - \frac{\phi_{1T}}{\phi_0 e^{-\alpha l_1}} \qquad (5)$$

To determine the effects of light power on the transmittance, a test was performed to validate the hypothesis that the attenuation coefficient or transmittance is not affected by the strength of the incoming light power. The light with different intensities was applied to the same sample. The optical intensity was adjusted from low to high within the power range under 9 mW/cm$^2$ and the transmittances were recorded and compared.

Once the transmittance of individual tissue was determined, the transmittance of combined tissues was estimated using the Beer-Lambert law. A validation test was performed to prove the hypothesis that the transmittance of a tissue combination is equal to the product of each individual rate with the surface loss effect taken into consideration. The hypothesis can be represented by the following equation.

$$T_c' = \frac{\phi_{2T}}{\phi_0} = (1-r_1)e^{-\alpha_1 l_1}e^{-\alpha_2 l_2} \qquad (6)$$

Where $T_c'$ is the transmittance of the combined tissues; $r_1$ is the surface loss rate of the tissue sample 18 which is in the front (i.e., nearest the light source); $\alpha_1$ and $\alpha_2$ are the attenuation coefficients of corresponding tissues; and $l_1$ and $l_2$ are the thicknesses of corresponding tissues.

To validate the hypothesis, the transmittances of two tissue combinations (gum and cortical bone, and cortical bone and trabecular bone) were measured, and then compared with the predicted transmittances that were calculated based on the transmittances of the corresponding single materials from the same animal using equation (6). The experiment consisted of sticking the two flat pieces of different tissue samples 18 together and measuring the transmittance.

To further validate the hypothesis, the transmittance of combined tissue samples consisting of gum, cortical bone, and trabecular bone in natural anatomy harvested from rats and pigs were tested and compared with the prediction. The thickness of each tissue in the rat sample was measured from the rat's micro-CT scan. The thickness of each tissue in the pig sample was measured using a caliper at the nearby sections. The thickness is uneven. Only an estimated average was used for each tissue.

Results

Figure 5:
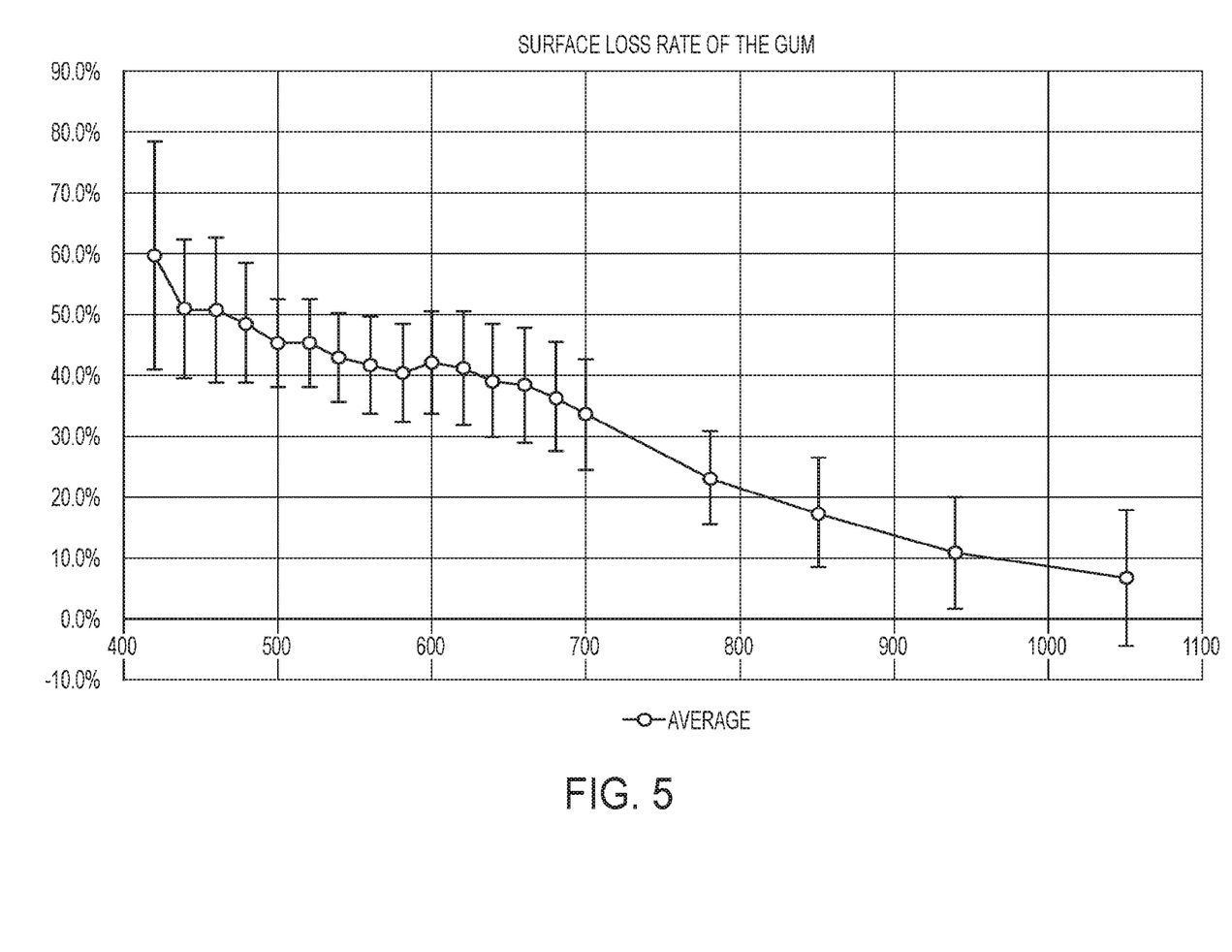
FIG. 5 is a graph showing surface loss rate of gum tissue.

A portion of the light power was lost at the gum surface. The surface loss rate (y-axis) as a function of the source light wavelength (x-axis) is shown in FIG. 5. The surface loss significantly reduced as the wavelength approached 1050 nm.

Figure 6:
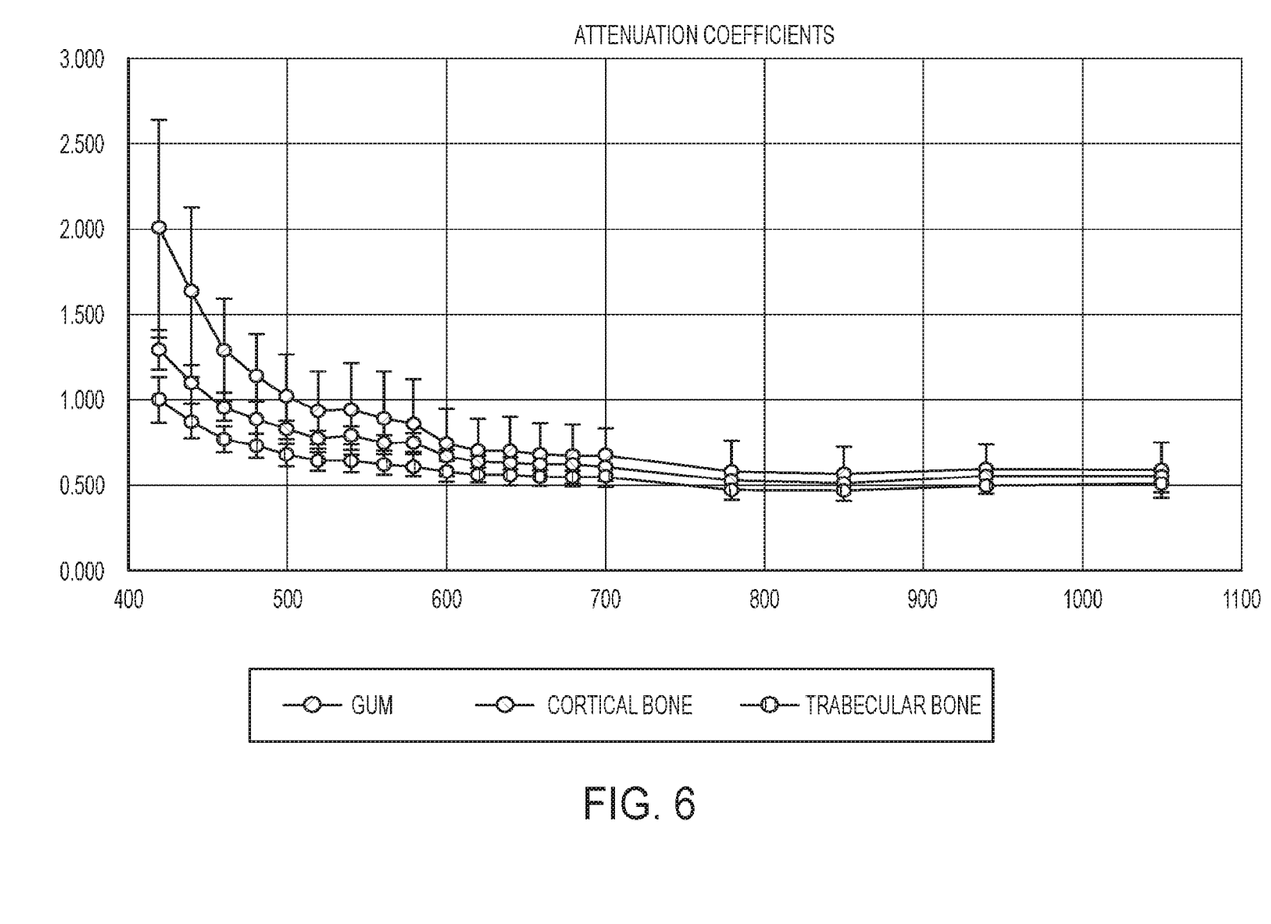
FIG. 6 is a graph showing attenuation coefficients of gum tissue, cortical bone and trabecular bone.

The results also show that transmittance in terms of attenuation coefficient also depends on the wavelength of the light source. As shown in FIG. 6, higher coefficients occur at shorter wavelengths. The attenuation coefficient values plateaued with wavelengths exceeding 700 nm. FIG. 6 shows the attenuation coefficients of the gum, cortical bone, and trabecular bone samples 18. At all wavelengths tested, the gum has the highest attenuation coefficient, while the trabecular bone has the lowest.

Figure 7:
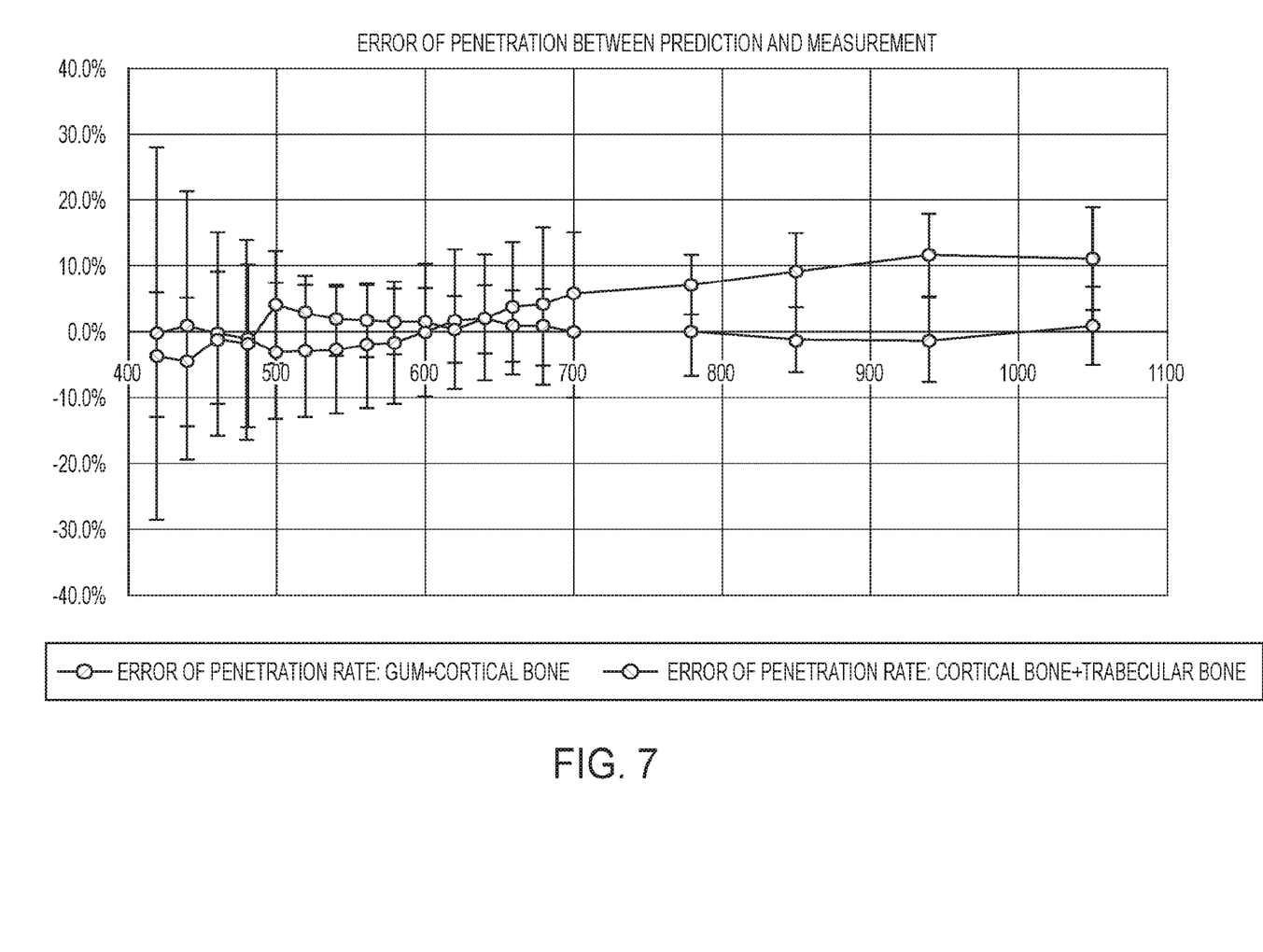
FIG. 7 is a graph showing error of penetration compared to measurement for tissue combinations of gum and cortical bone and cortical bone and trabecular bone.

The Beer-Lambert Law was applied to estimate the transmittance of a combination of two different tissues. The law was validated experimentally. The errors of transmittance at different wavelengths of two different combinations (i.e., cortical bone and gum and cortical and trabecular bone) are shown in FIG. 7. The latter has lower error overall.

Figure 8:
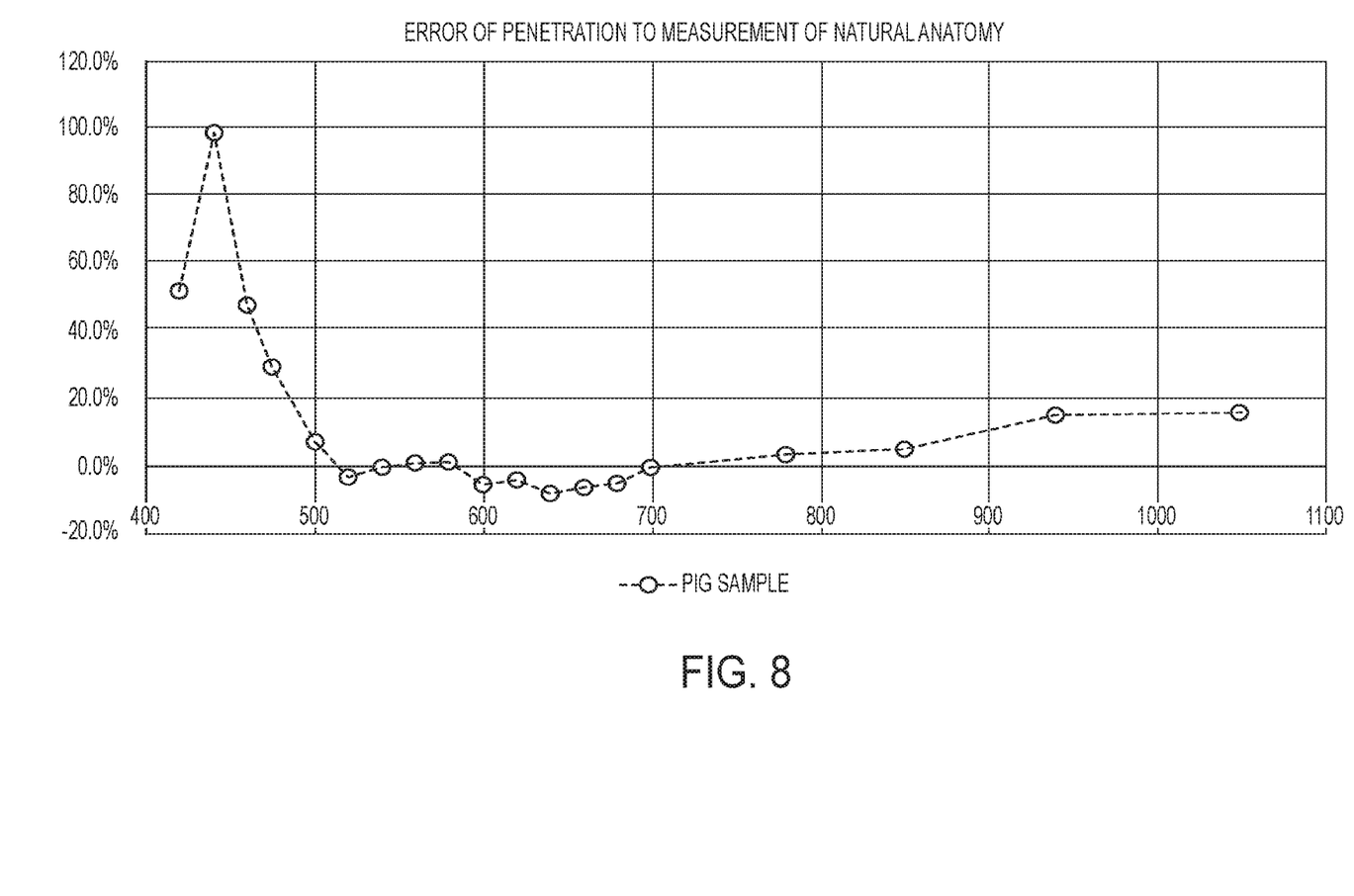
FIG. 8 is a graph showing error of penetration to measurement of natural anatomy on a pig.

Referring now to FIG. 8, the combination of three tissues in their natural anatomy was tested on pig tissue. The results show that the error can be large at lower wavelengths (below approximately 500 nm), and is acceptable at higher wavelengths (above approximately 500 nm).

The effects of light power on the transmittance were also evaluated at different wavelengths using different tissues. Table 1 shows the results of the transmittance versus light intensity. Three pieces of cortical bone, one trabecular bone, and one gum were tested under two wavelengths of light (940 nm or 780 nm). With the lighting intensity ranging from 0.3 to 8.8 mW/cm$^2$, the transmittances have negligible changes (<3.5%).

The transmittance of combined tissues was estimated using the Beer-Lambert law (see FIG. 7). The law was tested experimentally by stacking two tissue samples together. The transmittances of the combined tissues were measured and predicted based on the rate of individual tissue of the same animal. The error of prediction in the gum and cortical bone group was larger than that in the cortical and trabecular bone group. However, the average error did not exceed 11.7%, which is still acceptable, meaning that the law is valid. While not being limited to any particular theory, the error and variation could come from two factors: 1) the gum was soft tissue, thus the shape could slightly change while attaching the sample to the meter, and it is also difficult to align the gum to the meter; and 2) minor surface loss might occur at the interface of two tissues as they had different attenuation coefficients.

The law was further tested on samples of pig with all three tissues included in natural anatomy (see FIG. 8). The sample was randomly selected from the ten pigs, and the average attenuation coefficients of all the pigs were used for prediction. The tissue thickness in the pig sample was not even.

TABLE 1

Transmittance/intensity test

| Power (μW/cm$^2$) 940 nm light | Cortical 1 | Power (μW/cm$^2$) 940 nm light | Cortical 2 | Power (μW/cm$^2$) 780 nm light | Cortical 3 | Power (μW/cm$^2$) 940 nm light | Gum | Power (μW/cm$^2$) 780 nm light | Trabecular |
|---|---|---|---|---|---|---|---|---|---|
| 310 | 32.0% | 586 | 32.3% | 1281 | 29.4% | 413 | 29.3% | 1005 | 18.0% |
| 840 | 30.9% | 854 | 33.8% | 1770 | 30.3% | 923 | 28.7% | 1642 | 17.8% |
| 1206 | 29.5% | 1178 | 33.7% | 2432 | 31.1% | 1467 | 29.1% | 2455 | 17.9% |
| 1881 | 31.5% | 1633 | 33.1% | 3100 | 30.7% | 2129 | 28.7% | 3589 | 18.4% |
| 1950 | 31.2% | 2184 | 32.7% | 3699 | 30.5% | 2563 | 29.1% | 5027 | 17.8% |
| 2824 | 33.1% | 3038 | 32.1% | 4788 | 30.7% | 3376 | 29.2% | 6048 | 17.8% |
| 3575 | 30.7% | 3782 | 33.5% | 6048 | 30.4% | 6510 | 28.6% | 7256 | 18.2% |
| 4795 | 30.9% | 6131 | 32.9% | | | 8797 | 29.1% | | |
| 5298 | 30.9% | | | | | | | | |
| 6131 | 30.9% | | | | | | | | |
| Correlation | −0.091 | Correlation | −0.127 | Correlation | 0.353 | Correlation | −0.212 | Correlation | 0.147 |

Discussion

Transmittances of light with different wavelengths on gum, cortical bone and cancellous bone were tested. The transmittances were characterized by attenuation coefficients so that the tissue thickness would not be a factor, equation (1). The higher the attenuation coefficient, the lower the transmittance will be.

As shown in FIG. 5, the attenuation coefficient of the three different tissues and surface loss of the gum were determined for the light with its wavelength in the range of 420 to 1050 nm. Gum has the highest attenuation coefficient among the three tissues, meaning highest light power reduction. The trabecular bone has the lowest attenuation coefficient, which allows more light to penetrate through.

All samples showed higher transmittance using light with longer wavelengths. The difference is significant. For example, assuming the tissue thickness is 1 mm and the average attenuation coefficient of gum for the 420 nm and 1050 nm wavelength light is 2.01 and 0.586, respectively, and the corresponding surface loss rate is 59.9% and 6.7% respectively, then the transmittances from the equation (1) are (1-59.9%)×13.4%=5.4% and (1-6.7%)×55.7%=52% (10 times), meaning much more light can transmit through the tissue at longer wavelengths. The attenuation coefficient plateaued for the light with wavelengths between 700 nm to 1050 nm, meaning the transmittance with in this range is similar.

Only the average thickness was used, thus the error is inevitable. As shown in FIG. 8, the error is large at lower wavelengths. The reason is that the attenuation coefficients of the three tissue samples were very different and high at lower wavelengths. Thus the prediction at lower wavelengths was very sensitive to the thickness of each tissue, which cannot be accurately measured. The error at higher wavelengths was much lower, which is within the variation of the prediction shown in FIG. 7, and thus, is acceptable. The error at higher wavelength can be further reduced if compensation was made based on the error shown in FIG. 7.

The transmittance was not affected by the optical strength or light intensity (See Table 1). There was no correlation between the light intensity and the transmittance. The variation is within 3.5%, which is relatively small (~10% of the transmittance).

Based on the results discussed above, higher wavelengths of 780 to 1050 nm had a higher transmittance and more reliable optical power prediction. If wavelength is not a critical factor to PBM, wavelengths from 780 to 1050 nm can be a good choice for the light source.

It should be understood that the minor blood which should be residual in the trabecular bone could not be maintained during the sample preparation. Thus the true attenuation coefficient of trabecular bone in living pigs could be slightly higher than the results discussed herein.

CONCLUSIONS

Based on the foregoing, the following conclusions may be reached:
1) Within the wavelength range of 420 to 1050 nm, longer wavelengths lead to lower attenuation coefficients or higher transmittances;
2) Light intensity does not affect the transmittance in the intensity range of about 0.3 to about 8.8 mW/cm$^2$; and
3) The Beer-Lambert law with the surface loss effect taken into consideration can be used to estimate the transmittance for multiple tissue complex.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus While the embodiments have been described as having exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this invention pertains.

We claim:

1. A method for determining a transmittance of light on tissue, comprising:
   providing a light source;
   directing light from the light source onto a sample of tissue;
   measuring a first power of the light at a first surface of the sample;
   measuring a second power of the light at a second surface of the sample;
   computing a surface loss of the light; and
   determining the transmittance of the light using the first power, the second power, and the surface loss.

2. The method of claim 1, wherein the transmittance of light is represented by an attenuation coefficient in the Beer-Lambert law.

3. The method of claim 2, wherein determining the transmittance includes computing the transmittance according to $$T = \frac{\phi_T}{\phi_0} = (1-r)e^{-\alpha l}$$

where T is the transmittance without the surface loss, $\phi_T$ is a radiant flux of the second power of the light at the second surface of the sample, $\phi_0$ is an incoming radiant flux, r is the surface loss rate, $\alpha$ is the attenuation coefficient, and l is a thickness of the sample.

4. The method of claim 3, wherein the first surface of the sample is directed toward the light source and the second surface of the sample is directed away from the light source.

5. The method of claim 1, wherein the light source is one of an LED or a laser.

6. The method of claim 1, wherein the tissue is oral tissue.

7. The method of claim 1, wherein directing light from the light source includes directing light having a wavelength between about 420 nm and about 1050 nm.

8. A system for determining a transmittance of light on tissue, comprising:
   a light source that emits light;
   a wavelength meter having an input window, the wavelength meter being configured to measure a first power of the emitted light at a first surface of a sample of the tissue positioned at the input window and a second power of the emitted light at a second surface of the sample; and
   a controller coupled to the wavelength meter, the controller being configured to collect data to compute a surface loss rate of the emitted light onto the sample and to determine the transmittance of the emitted light into the sample using the first power, the second power and the surface loss rate.

9. The system of claim 8, further comprising a spectroscope having an input to receive light from the light source and output that emits the emitted light at a desired wavelength.

10. The system of claim 9, wherein the light source is one of an LED or a laser that emits light at a wavelength below about 1050 nm.

11. The system of claim 8, wherein the controller computes the transmittance according to $$T = \frac{\emptyset_T}{\emptyset_0} = (1-r)e^{-\alpha l}$$

where T is the transmittance without the surface loss, $\emptyset_T$ is a radiant flux of the second power of the light at the second surface of the sample, $\emptyset_0$ is an incoming radiant flux, r is the surface loss rate, $\alpha$ is an attenuation coefficient, and l is a thickness of the sample.

12. The system of claim 8, wherein the first surface of the sample is directed toward the light source and the second surface of the sample is directed away from the light source.

* * * * *